United States Patent [19]
Sarian et al.

[11] Patent Number: 5,183,039
[45] Date of Patent: Feb. 2, 1993

[54] TEMPERATURE CONTROL DEVICE FOR FLUID FILLED PAD

[75] Inventors: Grigor Sarian, Los Angeles; Barry R. Crandall, Saugus; Jeff R. Duncan, Sepulveda, all of Calif.

[73] Assignee: Baxter International Inc., Deerfield, Ill.

[21] Appl. No.: 749,092

[22] Filed: Aug. 23, 1991

[51] Int. Cl.⁵ ............................ A61F 7/00; H05B 1/02
[52] U.S. Cl. ..................... 128/400; 128/399; 165/46
[58] Field of Search ............ 128/399, 400, 402; 165/46

[56] References Cited

U.S. PATENT DOCUMENTS

| | | | |
|---|---|---|---|
| 2,198,989 | 3/1937 | Cooley | 128/254 |
| 2,215,042 | 3/1939 | Howard et al. | 219/46 |
| 3,074,410 | 1/1961 | Foster | 128/400 |
| 3,894,213 | 7/1975 | Agarwala | 128/400 |
| 3,967,627 | 7/1976 | Brown | 128/400 |
| 4,102,199 | 7/1978 | Tsipouras | 73/362 AR |
| 4,122,719 | 10/1978 | Carlson et al. | 73/342 |
| 4,161,880 | 7/1979 | Prosky | 73/342 |
| 4,356,383 | 10/1982 | Dahlberg et al. | 165/46 |
| 4,459,468 | 7/1984 | Bailey | 128/400 |
| 4,772,778 | 9/1988 | Ogawa | 165/46 |
| 4,844,072 | 7/1989 | French et al. | 128/400 |
| 4,966,145 | 10/1990 | Kikumoto et al. | 128/399 |
| 5,097,829 | 3/1992 | Quisenberry | 128/400 |

Primary Examiner—Jessica J. Harrison
Attorney, Agent, or Firm—Kay H. Pierce; Paul C. Flattery; James Henricks

[57] ABSTRACT

A control circuit for a fluid-filled heating pad is described. The control circuit is unique in that it includes a thermistor that is located in close proximity to the heating pad. The circuit is also unique in that it includes a single high-precision reference resistor to self-calibrate the control circuitry.

4 Claims, 3 Drawing Sheets

TEMPERATURE CONTROL DEVICE FOR FLUID FILLED PAD

BACKGROUND OF THE INVENTION

1. Field of the Invention

The invention relates generally to fluid-filled heating pads and more specifically to control circuitry for maintaining a desired temperature of fluid in such fluid-filled heating pads.

2. Brief Description of the Prior Art

Water-filled heating pads are generally used in hospitals because they are considered to be relatively safe and efficient. One fluid-filled heating pad currently on the market is sold by Baxter Healthcare Corporation. This heating pad includes a control module that is connected to a pad by a pair of tubes. Water is heated in the control module and is circulated through the tubes to the pad. A thermistor located in the control module monitors the temperature of the fluid within the module.

If the distance between the module and the pad is relatively short, the temperature in the pad is approximately equal to the temperature in the module. However, if the distance is significant, or if the tubes connecting the pad to the module are exposed to significant temperature drops, the fluid in the pad may be significantly lower than the temperature of the fluid within the module. Therefore, it is desired to provide a more accurate means of monitoring the temperature of the fluid in the pad.

All fluid-filled heating pads in which the fluid is electronically heated require a means of calibrating whatever temperature monitoring device is used. As discussed above, thermistors that are located in a control module have been used in the past to monitor the temperature of fluid in a remotely located heating pad. Such thermistors generate a nonlinear signal which needs to be calibrated in order to correlate the thermistor signal to the temperature of the fluid.

Earlier versions of electronically heated fluid-filled pads using such thermistors were calibrated using one or more potentiometers. These potentiometers were typically adjusted by a manufacturer during the manufacture of a regulator module to individually modify the output signal from each thermistor in order to correlate that thermistor's output signal to a given temperature range. This meant that each thermistor had to be manually calibrated during the manufacturing process. More recently, self-calibrating electronic circuits have been developed which do not require the manufacturer to calibrate each unit individually. In a self-calibrating unit, two high-precisions reference resistors are used to provide a "two-point calibration."

The two reference resistors are used to measure and calibrate the current generator which, in turn, is used to measure the resistance of the temperature measuring thermistor. The measured and calibrated current is applied to the thermistor. A voltage, caused by the current, is developed across the thermistor. The voltage across the thermistor is directly proportional to the resistance of the thermistor.

The resistance of a thermistor is inversely proportional to its temperature. Thus as the temperature of the thermistor decreases, the resistance of the thermistor increases, and as the temperature of the thermistor increases, the resistance of the thermistor decreases. Accordingly, the resistance of a thermistor (and through additional calculations its temperature) can be calculated by dividing the voltage developed across the thermistor by the amount of current passing through the thermistor.

The resistance of a thermistor is an indication of the temperature of the thermistor, and the resistance of a thermistor ($R_{thermistor}$) can be calculated as follows:

$$R_{thermistor} = \frac{V_{thermistor}}{I_{thermistor}}$$

where:

$V_{thermistor}$ = the voltage across the thermistor, and
$I_{thermistor}$ = the current through the thermistor.

Thus, any error in measuring the current through the thermistor produces an error in determining the temperature of the thermistor.

While the use of a "two-point" calibration method is an accurate way of measuring and calibrating the current generator, a need existed to reduce the complexity of the circuits and calculations used in a control module for a fluid-filled heating pad, yet maintain the necessary precision and overall accuracy of measuring the temperature of a fluid over the very limited temperature range of interest using the resistance temperature characteristics of a thermistor. Therefore, it is an object of the invention to eliminate one of the resistors to reduce the complexity of the electronic circuitry. It is also an object of the invention to provide a thermistor in close proximity to the fluid in the heating pad to be able to more accurately monitor the temperature of the fluid in the pad.

SUMMARY OF THE INVENTION

A device for heating fluid to be delivered to a fluid-filled heating pad is described. The device includes a temperature regulator module, a pad, and a pair of tubes for transporting fluid between the tank and the pad. Each of the tubes includes first and second ends in which each of the first ends is connected to the temperature regulator module and each of the seconds ends is connected to the fluid-filled heating pad so that fluid may flow between the pad and the regulator module.

The regulator module includes: (1) a tank containing fluid to be heated; (2) a pump for pumping fluid in the tank to the pad; and (3) temperature control circuitry for monitoring and regulating the temperature of fluid in both the tank and the pad.

The temperature control circuitry comprises: (1) a microprocessor; (2) heater means for heating fluid in the tank; (3) a remote thermistor for measuring the temperature of the fluid at the pad; (4) a constant current generator that generates a precision current; and (5) a tank thermistor for sensing the temperature of the fluid in the tank. The remote and tank thermistors are connected to the constant current generator.

The temperature control circuitry also includes a high-precision reference resistor that is also connected to the constant current generator. The reference resistor generates a predetermined, high-precision voltage signal. The subject invention involves the recognition that a pseudo-reference point can be used as one of two points of a "two-point" calibration, provided that the second point or pseudo-reference point is the zero resistance, and therefore, the zero voltage point.

The temperature control circuitry further includes a switching network that is connected to the microprocessor. The purpose of the switching network is to sequentially connect the precision constant current generator to each of: (1) the tank thermistor; (2) the remote thermistor; (3) the high-precision reference resistor; and (4) the remote thermistor and the reference resistor in parallel. The switching network sequentially applies the precision constant current to each of the above resistor or thermistor elements to produce a voltage output signal that is proportional to each of the individual resistive elements.

An analog-to-digital converter is also provided that is connected to the voltage output signal to convert the voltage output signal into a digital output signal. The digital output signal is then sent to the microprocessor. The microprocessor uses the digital output signal from each of the reference resistor, and the tank and remote thermistors to calculate the temperature of the fluid in the tank and the temperature of the fluid at the remote thermistor. The temperature of the fluid is displayed. The microprocessor compares the temperature of the fluid to a setpoint temperature and controls the heater accordingly. If the temperature of the fluid is below the setpoint temperature, the heater is turned on. If the temperature of the fluid is above the setpoint value, the heater is turned off.

DETAILED DESCRIPTION OF THE PREFERRED EMBODIMENT

Figure 1:
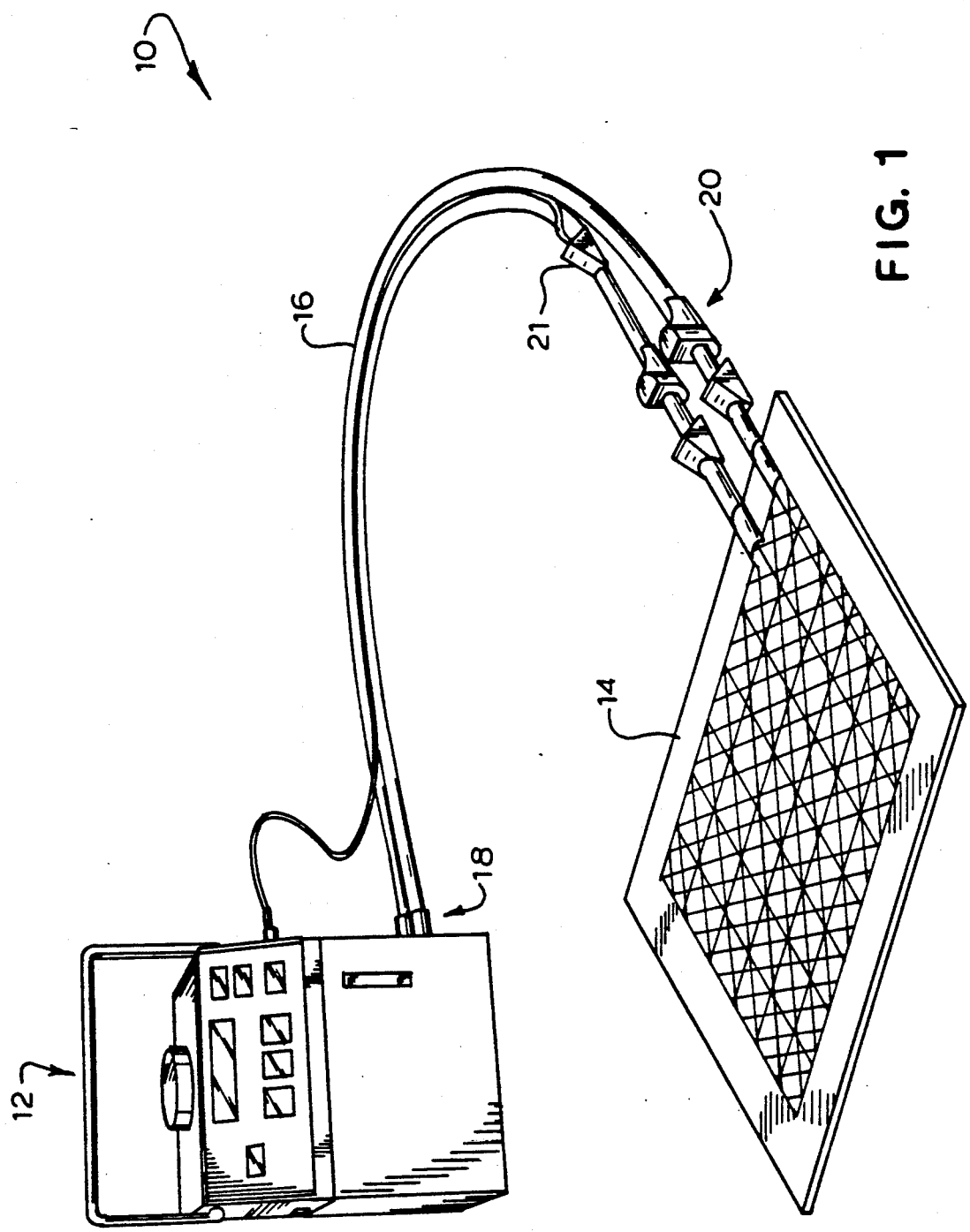
FIG. 1 is an isometric view of a fluid-filled heating pad.

Refer now to FIG. 1 which is a schematic diagram of a fluid-filled heating pad device 10. The device includes a temperature regulator module 12 that is connected to a fluid-filled heating pad 14 through a pair of tubes 16. One of the tubes 16 transports fluid to the pad 14 while the other of the tubes transports fluid from the pad to the regulator module 12. The tubes each include first and second ends 18, 20 respectively. The first end 18 of each tube is connected to the temperature regulator module 12. The second end 20 of each tube is connected to the fluid-filled heating pad 14 so that fluid may circulate between the pad and the regulator module.

In the preferred embodiment of the invention, a remote thermistor 21 is connected to the second end 20 of one of the tubes. The remote thermistor 21 senses the temperature of the fluid in the second end of one of the tubes. Since the second end of each of the tubes is in close proximity to the fluid-filled pad 14, the remote thermistor 21 provides an accurate reading of the temperature of the fluid in the pad. Although in the preferred embodiment of the subject invention, the remote thermistor is located at the second end of one of the tubes, in other embodiments, the remote thermistor may be actually located on the pad 14.

Figure 2:
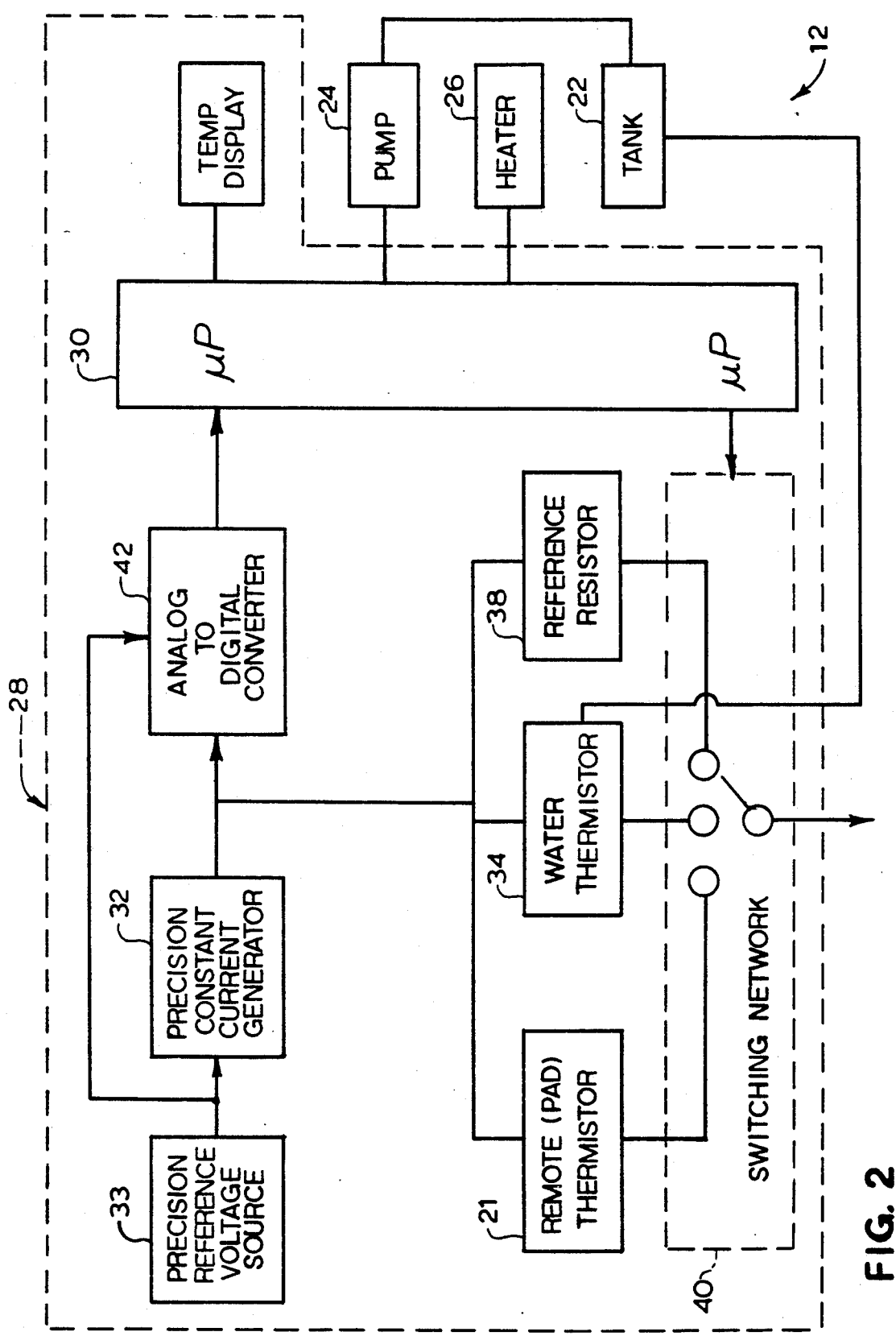
FIG. 2 is a block diagram of the temperature regulator module.

Refer now to FIG. 2 which is a block diagram of the temperature regulator module 12. As can be seen in the figure, the regulator module 12 includes a tank 22 that contains fluid to be pumped to pad 14. The regulator module 12 also includes a pump 24 to pump water in the tank through one of the tubes to the pad 14. The module 12 also includes a heater 26 for heating the fluid in the tank.

The regulator module 12 still further includes temperature control circuitry 28 for monitoring and maintaining the temperature of the fluid in the pad 14 at a desired temperature. The control circuitry 28 includes a microprocessor 30 that is connected to the heater means 26. The microprocessor controls the delivery of current to the heater means 26 and causes the heater to heat the fluid in the tank 22 to a desired temperature.

The control circuitry 28 also includes a precision constant current generator 32 which receives a voltage from a precision reference voltage source 33. A tank thermistor 34 is also included in the control circuitry to sense the temperature of the fluid in the tank. The tank thermistor 34 and remote thermistor 21 are connected to the constant current generator 32 to receive current from the current generator.

A high-precision reference resistor 38 is also provided in the temperature control circuitry 28. The reference resistor 38 is also connected to the constant current generator 32 so that the resistor 38 can generate a predetermined, high-precision reference voltage signal.

The temperature control circuitry 28 still further includes a switching network 40 that is connected to the microprocessor 30. The microprocessor directs the switching network to sequentially connect the constant current generator 32 and an analog-to-digital converter 42 to the output voltage signals from each of: (1) the remote thermistor 21; (2) the tank thermistor 34; and (3) the reference resistor 38. The analog-to-digital convertor converts the output voltage signals from an analog to a digital signal which can be transmitted to the microprocessor 30.

The microprocessor 30 calculates the temperature of the fluid in the tank 22 and at the remote pad 14, using the measured voltage across: (1) the precision reference resistor 38, (2) the tank thermistor 34, and (3) the remote thermistor 21. The method by which the microprocessor determines the temperature of the fluid in the tank and pad is set forth in greater detail below.

The reference voltage measured across the reference resistor and the pseudo-reference point (zero volts, zero resistance) are calculated by the microprocessor and are used to produce a "pseudo-two-point calibration".

The reference voltage, measured across the reference resistor, minus the pseudo-reference voltage, (zero volts), divided by the resistance of the reference resistor minus the pseudo-reference resistance, (zero ohms), is a measure of the magnitude of the current generated by the precision constant current generator. Using this precision current as indicated by the reference voltage, the ratio of the reference voltage to the voltage of each of the thermistor elements is used to determine the temperature of both the tank fluid and fluid in the pad.

The temperature of the water in the tank and the pad is determined by monitoring the resistance of the tank and remote thermistors since a thermistor's resistance is proportional to actual temperature. In the preferred embodiment of the subject invention, the resistance ($R_{thermistor}$) of each of the tank and remote thermistors is determined by multiplying the known quantity of the reference resistance ($R_{ref}$) by the voltage across the thermistor ($V_{thermistor}$) and dividing the result by the voltage across the reference resistor ($V_{ref}$). It should be noted that $V_{ref}$ is directly proportional to the precision constant current.

$$R_{thermistor} = \frac{R_{ref}V_{thermistor}}{V_{ref}}$$

The voltage across the reference resistor, minus the pseudo-voltage point, (zero volts), is proportional to the precision constant current. The overall circuit does not need any adjustment because self calibration is achieved through the recognition that the current through $R_{thermistor}$ is the same as $R_{ref}$.

One of the problems in using a thermistor to measure temperature is that a method is needed to insure that the thermistor is properly working. The subject invention provides a method of discrimination between the out-of-range high resistance of a very cold thermistor due to very cold fluid and the out-of-range high resistance of an open circuit or disconnected thermistor. This is accomplished by connecting the thermistor and the reference resistor to the constant current generator simultaneously. The two resistances together produce a parallel resistance circuit within the measurement range.

The voltage across the parallel combination of the resistor pair is measured and compared to a predetermined threshold value. If the measured voltage exceeds the predetermined value, the thermistor is considered to be either open-circuit disconnected, or otherwise inoperable. By putting the elements in parallel and measuring the voltage across both elements (as opposed to measuring the voltage across the thermistor alone), the dynamic range for open-circuit discrimination versus very cold fluid is increased.

Figure 3:
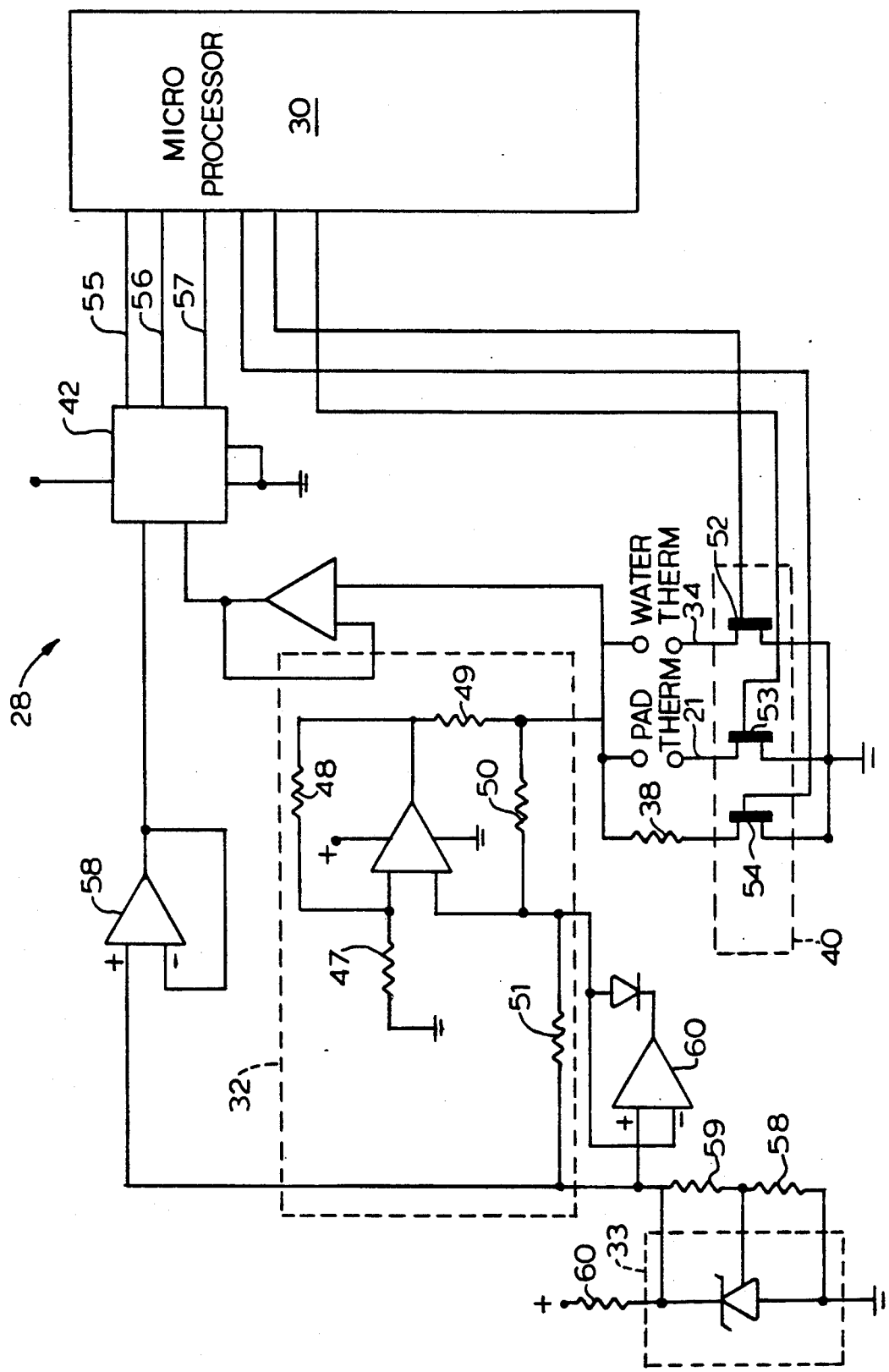
FIG. 3 is a schematic diagram of the block diagram of FIG. 2.

Refer now to FIG. 3 which is a circuit diagram of the control circuitry. The precision constant current generator 32 includes operational amplifier 46 and resistors 47-51. Resistors 47, 48, 50 and 51 set the gain of the amplifier 46 while resistor 49 sets the output current of the constant current source. The switching network 40 includes FET switches 52-54 which sequentially connect reference resistor 38, remote thermistor 21 and tank thermistor 34 to the constant current generator 32. The analog-to-digital convertor 42 includes a ten-bit a/d convertor with an integral analog multiplexer. The data is transmitted to the microprocessor 30 through serial ports 55-57. It is important to note that the precision voltage source 33 applies the same voltage to both the constant current generator 32 and the analog to digital convertor 42. This eliminates the introduction of an error. The voltage is applied to the analog-to-digital convertor 42 through buffer 58 and to the constant current generator 32 through buffer 60. Resistors 58-60 are used to adjust the voltage of voltage source 33.

While the invention has been described in detail and with reference to specific embodiments thereof, it will be apparent to those skilled in the art that various changes and modifications can be made therein without departing from the spirit and scope of the invention.

We claim:

1. A device for heating fluid to be delivered to a patient comprising:
   a temperature regulator module having a tank containing fluid, a pump, and temperature control circuity;
   a fluid-filled heating pad;
   tubing for transporting fluid, said tubing having a first and second ends, said first end connected to said temperature regulator module, said second end connected to said fluid-filled heating pad, so that fluid may flow between said pad and said regulator module;
   a remote thermistor adjacent the heating pad and oriented relative to the tubing for measuring the temperature of said fluid at said pad; and
   said temperature control circuitry having;
   a microprocessor;
   heater means for heating fluid in said tank;
   a precision constant current generator;
   a precision voltage reference;
   a tank thermistor for sensing the temperature of fluid in said tank, said tank thermistor being coupled to said precision constant current generator to receive current;
   electrical connector means for coupling said remote thermistor to said temperature control circuitry, said connector means also coupled to said precision constant current generator to supply a fixed, precision, and constant current to said remote thermistor;
   a high-precision reference resistor also coupled to said precision constant current generator, said resistor generates a high-precision single point reference voltage signal;
   a switching network coupled to said microprocessor, to sequentially couple said microprocessor to each of
   said high-precision reference resistor
   said tank thermistor, and
   said remote thermistor,
   to produce a precision voltage output signal from each;
   an analog to digital convertor coupled to said precision voltage output signal and to said microprocessor, to convert said precision voltage output signal into a digital signal for said microprocessor; and
   a precision and stable reference voltage source coupled to said constant current generator to cause said current generator to produce a precision constant current and coupled to said analog-to-digital convertor to drive said convertor.

2. A device for heating fluid to be delivered to a patient comprising:
   a temperature regulator module having a tank containing fluid, a pump, and temperature control circuitry;
   a fluid-filled heating pad;
   tubing for transporting fluid, said tubing having first and second ends, said first ends connected to said temperature regulator module, said second ends connected to said fluid-filled heating pad, so that fluid may flow between said pad and said regulator module;
   a remote thermistor adjacent the heating pad and oriented relative to the tubing for measuring the temperature of said fluid at said pad;
   a tank thermistor for sensing the temperature of fluid in said tank, said tank thermistor and said remote thermistor being coupled to said temperature control circuitry so that the temperature control circuitry can use the remote thermistor to control the temperature of the heating pad.

3. The device of claim 2 wherein the tubing includes an input tube for fluid to the heating pad and the remote thermistor is oriented relative to the input tube for measuring the temperature of said fluid being input to said heating pad.

4. The device of claim 2 further comprising a precision reference resistor and a switching network coupled to the temperature control circuitry for coupling the temperature control circuitry to the remote thermistor and the precision reference resistor in parallel.

* * * * *